US009345862B2

(12) United States Patent
Baid

(10) Patent No.: US 9,345,862 B2
(45) Date of Patent: May 24, 2016

(54) NEEDLE TIP PROTECTOR ASSEMBLY FOR SAFETY IV CATHETER ASSEMBLY

(75) Inventor: Rishi Baid, New Delhi (IN)

(73) Assignee: POLY MEDICURE LIMITED, Faridabad (IN)

( * ) Notice: Subject to any disclaimer, the term of this patent is extended or adjusted under 35 U.S.C. 154(b) by 0 days.

(21) Appl. No.: 14/235,202

(22) PCT Filed: Jul. 26, 2012

(86) PCT No.: PCT/IB2012/053820
§ 371 (c)(1),
(2), (4) Date: Jan. 27, 2014

(87) PCT Pub. No.: WO2013/014639
PCT Pub. Date: Jan. 31, 2013

(65) Prior Publication Data
US 2014/0163470 A1    Jun. 12, 2014

(30) Foreign Application Priority Data
Jul. 26, 2011    (IN) .......................... 2109/DEL/2011

(51) Int. Cl.
*A61M 25/06*    (2006.01)
*A61M 5/32*    (2006.01)

(52) U.S. Cl.
CPC ....... *A61M 25/0618* (2013.01); *A61M 25/0606* (2013.01); *A61M 5/3273* (2013.01); *A61M 2005/325* (2013.01)

(58) Field of Classification Search
CPC ............ A61M 25/06; A61M 25/0612; A61M 25/0618; A61M 5/3273; A61M 2005/325
USPC ............ 604/164.01, 164.06, 164.08, 165.01, 604/263, 272
See application file for complete search history.

(56) References Cited

U.S. PATENT DOCUMENTS 4,964,854 A    10/1990    Luther
5,718,688 A    2/1998    Wozencroft
(Continued)

FOREIGN PATENT DOCUMENTS

EP    1250943 A1    10/2002
EP    1297859 A2    4/2003
(Continued)

OTHER PUBLICATIONS

International Search Report; International Application No. PCT/IB2012/053820; Date of Actual Completion of International Search: Nov. 30, 2012; Date of Mailing of International Search Report: Jul. 12, 2012.

*Primary Examiner* — Theodore Stigell
*Assistant Examiner* — Amber Stiles
(74) *Attorney, Agent, or Firm* — Pearne & Gordon LLP

(57) ABSTRACT

The invention relates to a needle tip guard for a safety IV catheter assembly comprising a catheter tube having a distal end and a proximal end; a catheter hub having a distal end and a proximal end, wherein the distal end is joined to the said catheter tube and the proximal end defines a chamber; a needle extending through the catheter hub and the catheter tube having opposite proximal and distal ends defining an axial direction A, wherein the proximal end is joined to the needle hub and the distal end forms a sharp tip and a change in profile is provided between the proximal and distal ends of the needle; and a tip protector assembly movably arranged in between the catheter hub and needle hub on the needle such that the tip protector assembly is retained partially and/or completely in the chamber of the catheter hub and wherein the tip protector assembly is configured to entrap the needle tip upon withdrawal of the needle from the catheter hub.

23 Claims, 13 Drawing Sheets

(56) References Cited

U.S. PATENT DOCUMENTS

| | | | |
|---|---|---|---|
| 6,749,588 B1 * | 6/2004 | Howell | A61M 5/3273 604/110 |
| 2002/0169418 A1 * | 11/2002 | Menzi | A61M 25/0637 604/164.07 |
| 2004/0225260 A1 | 11/2004 | Villa et al. | |
| 2005/0277879 A1 * | 12/2005 | Daga | A61M 25/0618 604/110 |
| 2008/0097343 A1 | 4/2008 | Woehr | |
| 2008/0249478 A1 * | 10/2008 | Ishikura | A61M 25/0618 604/198 |
| 2011/0213307 A1 * | 9/2011 | Kawai | A61M 5/158 604/164.08 |
| 2012/0277679 A1 * | 11/2012 | Steube | 604/164.08 |

FOREIGN PATENT DOCUMENTS

| | | | | |
|---|---|---|---|---|
| EP | 2127692 A1 | 12/2009 | | |
| WO | WO 2010038471 A1 * | 4/2010 | | A61M 5/158 |
| WO | 2010061405 A2 | 6/2010 | | |
| WO | 2011036574 A1 | 3/2011 | | |
| WO | 2011154767 A1 | 12/2011 | | |

* cited by examiner

NEEDLE TIP PROTECTOR ASSEMBLY FOR SAFETY IV CATHETER ASSEMBLY

CROSS-REFERENCE TO THE RELATED APPLICATION

This application is the national phase of International Application No. PCT/IB2012/053820 filed on Jul. 26, 2012, which claims priority from Indian Patent Application No. 2109/DEL/2011 dated Jul. 26, 2011, the entire disclosures of which are incorporated herein by reference.

FIELD OF THE INVENTION

The present invention relates to a medical device such as, for example a safety intravenous (IV) catheter assembly. More particularly, the invention relates to a needle tip protector assembly for safety IV catheter assembly with improved safety means and mechanism that automatically covers the sharp tip of the needle after withdrawal of the needle from the catheter and catheter hub.

BACKGROUND OF THE INVENTION

An intravenous (IV) catheter assembly of this kind is generally known and, for example, used to administer fluid and/or medicine to a patient or to take blood from a patient.

Accidental needle sticks/pricks have become a major concern to health-care worker. It is well known and understood by healthcare workers that sharp surgical instruments, such as catheter needles, have a significant potential for harm to healthcare workers. During surgery, handling of these sharp instruments can lead to accidental sticks or puncture wounds exposing the healthcare worker to the infections such as AIDS and hepatitis. The chances of needle stick are increased during an emergency with several aspects require to be handled. Likewise, during disposal, an exposed needle point may be and usually is a threat to the medical waste handler.

Various safety IV catheter assemblies have been developed to automatically cover and shield the needle tip after its withdrawal from the patient. These assemblies have taken a number of embodiments and have various degrees of elaboration. However, the safety mechanisms implemented in these assemblies increase costs of manufacture substantially and may malfunction, especially in a fluid-filled environment where it may stick or slip. Some of the known needle protecting systems requires multiple parts, which drives up the manufacturing cost for a disposable unit. The cost-benefit requirements of the medical industry call for an inexpensive needle protecting system which is disposable along with the needle. Furthermore, the system must be quick and easy to use as to present as little in position as possible to the administration and function of the safety IV catheter assembly.

Moreover, some IV catheter assemblies with the needle guard that have been developed sometimes fail to prevent occurrence of unintended needle stick injuries. Generally, in such assemblies a needle safety device or needle guard is arranged completely in a chamber defined by the catheter hub. In order to ensure correct protective function of the needle guard, it is necessary that the needle guard is secured steadily in its ready position while being secured inside in the catheter hub. However, such assemblies suffers from the problem of premature release of the needle guard from the catheter hub under retracting forces applied on the needle while disengaging the needle hub from the catheter hub. In such a situation, the tisk of accidental needle stick injury is a real threat to the users/practitioners. Moreover, such premature release and unsteadiness of the needle guard in the catheter hub affects its correct and effective function protecting the tip of the needle.

There is need to protect the healthcare workers from accidental needle pricks. Thus, there is a constant need for having a tip protector assembly for a safety IV catheter assembly with improved safety means that automatically covers the sharp tip of the needle after withdrawal of the needle from the catheter and catheter hub preventing accidental pricks and sticks and which is easy and inexpensive to manufacture.

OBJECTS OF THE INVENTION

Therefore, it is an object of the invention to provide a protective system which is simple and dependable in its deployment, inexpensive to manufacture, expedient in its operation and effective in protecting a needle tip, and which ensures correct functioning even after longer shelf life.

Other objects and advantages of the present invention can be ascertained from the following disclosure.

SUMMARY OF THE INVENTION

The present invention relates to a needle tip protector assembly for use in a safety in-travenous (IV) catheter assembly with improved safety means and mechanism that automatically covers the sharp tip of the needle after withdrawal of the needle from the catheter tube and catheter hub.

According to one embodiment, a safety IV catheter assembly is provided comprising: a catheter tube having a distal end and a proximal end; a catheter hub having a distal end and a proximal end, wherein the distal end is joined to the said catheter tube and the proximal end defines a chamber; a needle extending through the catheter hub and the catheter tube having opposite proximal and distal ends defining an axial direction, wherein the proximal end is joined to the needle hub and the distal end forms a sharp tip and a change in profile is provided between the proximal and distal ends of the needle; a tip protector assembly movably arranged in between the catheter hub and needle hub on the needle such that the tip protector assembly is retained partially and/or completely in the chamber of the catheter hub including: a base portion in the region of its proximal end having a needle passage with a through bore extending in an axial direction from a proximal side of the base portion to a distal side of the base portion; first and second arms extending substantially in the axial direction from the distal side of the base portion; at least one tension creating element surrounding partially and/or completely the said first and second arms in a region proximal to the distal ends thereof; at least one stopper element arranged in the base portion having an axial bore with a dimension adapted to the principal outer profile of the said needle; at least one pair of first and second retaining arms connected to the base portion by transverse segments extending therefrom in a direction opposing each other; and one or more first retaining means in an arrangement engaging with the one or more second retaining means provided on the inner and/or outer walls of the catheter hub for retaining the tip protector assembly in the chamber as long as the first arm is in its deflected state rests over the needle shaft.

The first and second retaining mms, thus, help to retain the first and second arms of the tip protector assembly in the catheter hub in its ready position prior to use preventing the premature release of the tip protector assembly from the catheter hub before the needle tip is safely received inside the first and second arms of the tip protector assembly.

According to an embodiment, the tip protector assembly is retained at least partially and/or completely inside and/or outside the catheter hub and is prevented from movement in the axial direction relative to the said catheter hub. The catheter hub is provided with second retaining means which may be provided inside and/or outside of the catheter hub for engaging and/or releasing the first retaining means provided in the tip protector assembly.

According to an embodiment, the needle can be moved through the catheter hub and the catheter tube when the tip protector assembly is in a ready position and to a tip protecting position in which the tip of the needle is fully received in the tip protector assembly and wherein a locking mechanism is provided to secure the tip protector assembly together with the catheter hub when the tip protector assembly is in its ready position.

According to an embodiment, the first arm and second arms of the tip protector assembly are provided with one or more first retaining means which is adapted to engage with the one or more second retaining means provided in the inner wall of the catheter hub which provides an additional safe and reliable engagement between the two components as long as the tip protector assembly is in its ready position. Thus, the present invention is also directed to a locking mechanism to secure steadily the tip protector assembly preventing any movement while it is retained with the catheter hub.

According to an embodiment, first retaining means provided on the first and second arms of the tip protector assembly include one or more retaining protrusions, for example disc-like retaining protrusion or annular disc like retaining protrusion or at least part annular disc like retaining protrusion or combination thereof provided in the region of the distal ends of the first and second arms. According to a preferred embodiment, the retaining protrusion is of part-circular, in particular semi-circular shape. More specifically, the retaining protrusion may have generally parallel proximal and distal faces and/or convex, in particular part-cylindrical, peripheral surface. The retaining protrusions are adapted to engage with second retaining means provided in the inner wall of the catheter hub. The second retaining means include one or more retaining depressions for example, a retaining recess/groove or annular retaining recess/groove or at least part annular recess/groove or combination thereof formed on the inner circumferential wall of the catheter hub. In an alternative embodiment, the first retaining means may be one or more depressions and second retaining means may be one or more protrusions. As a further alternative, the first and second retaining means may also be formed by a combination of one or more retaining protrusions and one or more retaining depressions.

According to an embodiment, the first retaining means provided on the first and second retaining arms include one or more retaining protrusions, for example hook or lug-like retaining protrusions adapted to engage with the second retaining means. In an alternative embodiment, the first retaining means may be formed by one or more retaining depressions, for example retaining recess/grooves. As a further alternative, the first retaining means may also be formed by a combination of one or more retaining protrusions and one or more retaining depressions.

According to an embodiment, the second retaining means provided on outer wall of the catheter hub include one or more retaining depressions, for examples, retaining recess/groove adapted to retain the first retaining means. In an alternative embodiment, the second retaining means may be formed by one or more retaining protrusions, for example hook or lug-like retaining protrusion. As a further alternative, the second retaining means may also be formed by a combination of one or more retaining protrusions and one or more retaining depressions.

According to an embodiment, the distal end of the transverse segments of the first and second retaining arms are angled and extend distally from the transverse segments and are slightly tilted towards the first and second arms forming an angle in the range between 0° to 10°. This angled extension and orientation of the first and second retaining arms provide restoration force and help the arms to act as springs having elastic properties thereby improving the retaining effect of the retaining arms with the second retaining means provided on the catheter hub. The first and second retaining arms engage with an outer surface of the catheter hub and help to retain the tip protector assembly in the catheter hub prior to use of the catheter, thus preventing the tip protector assembly from being removed from the catheter hub before the needle tip is safely received inside the tip protector assembly.

According to an embodiment, the first arm includes a first free end and the second arm includes a second free end extending generally axially in a distal direction from the base portion. The first free end extends beyond the second free end and overlaps the second free end by an angled end section including a length and width configured to retain the tip of the needle within a tip holding space so that in protected position the angled end section abuts the needle, in particular the tip of the needle. The length and width of the angled end section are larger than the maximum outer profile of the needle and/or its diameter and adapted to confine the needle tip within a tip holding space.

As a preferred alternative, angled end section of the first arm may have an undercut for catching the needle tip. Further, the portion forming the angled end section may be made of a second material different from the first material forming, for example the first and second arms of the tip protector assembly such that harder plastic material or portion reinforced with metal material or the like so that the needle abutting the angled end section cannot pierce through it and be retained firmly in the needle tip holding space even under application of excessive force.

According to an embodiment, each of the at least one side of the inner walls of the first and second arms of the tip protector assembly has internal recess close to the base portion thereof forming a cavity or cut out. The extension of the region above the said internal recess towards the distal end in the axial direction forms protective side-flaps in at least one side thereof providing an enclosure for the needle passing therethrough. The protective side-flaps provided on the first and second arms surround the needle shaft when passing through the first and second arms. The distal end of each of the internal recess in the first and second arms defines a shoulder. The side-flaps help prevent the needle tip from protruding sideways out of the tip protector assembly, thereby fluffier increasing the protective function thereof. Moreover, the internal recesses provided in the arms facilitate deflectability and also improves restoration capabilities thereof. In particular, the internal recess provided in the first arm helps in improving deflectability as well as the restoration properties of first arm when the distal angled end thereof is no longer supported on the needle shaft. Thus, the internal recess increases the deflectability of the arms in the regions it is provided and thereby reduces the restoring force acting thereon, in particular on the angled end section of the first arm while it is being supported by the needle shaft. This allows the needle to be moved more easily relative to the first and second arms and in particular relative to the angled end section, as the frictional force acting on the needle is reduced. In the embodiment, where a floating stopper element e.g. a floating disk or washer is provided as a stopper element the shoulder formed by distal end of the said internal recess in the first and second arms act as movement limiting means.

According to an embodiment, a tension creating element surrounds the first and second arms of the tip protector assembly, for example an elastic band in between the proximal and distal region of the first and second arms, in particular in a region proximal to the distal end of the first and second arms. The tension creating element exerts a restoring force on the first and second arms when tip protector assembly is in its ready position i.e. when the first and second arms are spread apart by the needle extending all the way through the tip protector assembly. Once the needle shaft no longer supports the angled end section of the first arm i.e. when the tip protector assembly is in its tip protecting position, the tension creating element aids the repositioning of the first arm back into axial alignment with the axial direction. This repositioning is necessary so that the angled end section can block the needle tip from axially sliding out of the tip protector assembly. In addition, the tension creating element defines a tip holding enclosure between the first and second arms and thus helps to prevent the needle shaft and the needle tip from protruding sideways out of the tip protector assembly. Thus, the tension creating element adds to the protective effect of the tip protector assembly by applying a radially confining biasing force.

In a preferred alternative, the tension creating element partly surrounds the first and second arms of the tip protector assembly i.e. instead of surrounding the two arms the tension creating elements biases the two arms by a linear biasing action.

In another preferred alternative, the tension creating element have the structure forming a link connecting the said first and second anus and which may be positioned and/or arranged in at least one of the either sides of first and second arms of the tip protector assembly.

In yet another preferred alternative, the tension creating element may have the structure forming a link connecting the said first and second arms and which may be positioned and/or arranged in both sides of first and second arms of the tip protector assembly.

In one embodiment, the tension creating element includes the structure in the form of a ring.

In one embodiment, the tension creating element may not be a separate component of the tip protector assembly and can be integrally made therein. It may be made from an elastic material and/or materials having elastic properties, for example, silicone, rubber or the like.

In one embodiment, the tension creating element may be arranged or positioned in any of the region in between the proximal and distal regions of the first and second arms of the tip protector assembly.

The change in profile may be defined as a needle section having a different dimension than the nominal diameter and may be created using various means. The change in profile may be for example, an enlargement and it may be made by crimping a portion of the needle either only on one side or point on the circumference of the needle or alternatively along both sides or symmetrically along the circumference of the needle.

In a preferred alternative, the change in profile may be formed in the form of a shoulder, bulge formed as an annular widening and by adding material onto the outer surface of the needle or by adding a sleeve to the needle for example, by welding, gluing or soldering etc. The added material may include a metal material, a plastic material, adhesive, resin or the like. In the case of the added material being metal material, the change in profile may, for example, be formed by build-up welding or by soldering of the additional material onto the needle. Alternatively, the additional material could be glued to the needle. The change in profile in the form of an enlargement may be referred to as a crimp, a sleeve, an annular sleeve, part annular sleeve, a bulge, a section of the needle with added material or combinations thereof. Further, the inner profile of the needle can either be reduced in the region of the change in profile, for example, if the change in profile is formed by crimping, or it can be substantially constant throughout the length of the needle, for example, if the change in profile is formed by applying additional material to the needle shaft.

In one embodiment, the needle shaft may also be formed with a slit forming an opening arranged distally or proximally from the change in profile therein. The opening may be formed by a small slit which is cut into the needle shaft and which extends in axial direction for a small distance, for example 0.3 to 1 mm. The opening is just large enough in order to provide an early blood flashback function close to the needle tip within the catheter tube such that the medical practitioner can recognize that needle has been placed correctly within the patient's vein. In case of correct, positioning of the needle, blood pours out of the opening within the needle shaft into the space between the needle shaft and the inner wall of the transparent catheter tube and visible to the medical practitioner.

In one embodiment, a groove may be provided either in the inner wall of one of the first and second arms extending substantially in the axial direction from the base portion. The groove acts as a guide groove for the needle shaft and aids the axial movement of the needle shaft relative to the tip protector assembly. Moreover, the needle shaft is prevented from sliding sideways, in particular off the angled end section of the first arm. Such a sideways movement would significantly increase the force required to move the needle shaft relative to the tip protector assembly, which would prevent a correct functioning of the tip protector assembly. Alternatively, the guide groove can be provided in both the first and second arms.

In one embodiment, the tip protector assembly is made from a unitary plastic material or, or an elastomer or thermoplastic or any combination thereof such as thermoplastic elastomer. In other embodiments, the tip protector assembly is made from multi-pieces and includes materials such as metal and/or plastic or any combination thereof. For example, either of the first and second arms or both may be made of a resilient material or plastic material or metal material or combination thereof.

In one embodiment, the stopper element is arranged within the base portion and can be integrally formed within the base portion of the tip protector assembly. The stopper element is made of a second material different from a first material of the base portion and has a through-bore with a profile which is adapted to the principal outer profile of the needle shaft. Preferably, the stopper element defines an axial bore having a cross-section adapted to the principal profile of the needle but being smaller than the radial dimension of the change in profile in the form of an enlargement forming the engagement means configured on the needle shaft. The stopper element is preferably arranged such that its axial-bore is in general alignment with the needle passage of the tip protector assembly.

According to an embodiment, the stopper element surrounds the needle. The length of the stopper element, i.e. its dimension seen in the axial direction, may vary. As such, the stopper element can, for example, be disk or a ring or a washer or a tube. However, it is to be understood that the outer profile of the stopper element does not have to have a circular outer profile. It is also possible that the outer profile of the stopper element is of non-circular form, for example, of oval or polygonal shape or other suitable geometric shape.

According to an alternative, it is also possible that the stopper element only partly surrounds the needle. In this case, the stopper element could have the shape of a slotted disk, ring or tube.

As yet another preferred alternative, the stopper element may also be arranged loosely on the needle between the two atms of the tip protector assembly and floating on the needle shaft and can be held in the area defined by the internal recess of the first and second al ins. As such the stopper element may be formed by a tube-like element. It can be held by holding means, like one or more retaining protrusions or retaining depressions in a predetermined section of the tip protector assembly, for example in a region proximal to the base portion of the tip protector assembly. Alternatively, the stopper element can be arranged in floating condition in a pre-determined section in between the first and second arms of the tip protector assembly anywhere in between the proximal section and distal section thereof along the line of needle passage configured therein.

To define the reference to first material and second material as used herein, preferably, the second material is of greater hardness and/or stiffness than the first material. For example, the first material could be a plastic material and the second material could consist of a metal, a harder fiber material, a rubber material or a ceramic, or any other type of suitable material which is stiff and not as easily distortable as the first material.

Yet another embodiment of the present invention relates to methods of making/assembling and using an IV catheter assembly including the tip protector assembly when the tip protector assembly is in its ready position.

Further advantageous embodiments of the invention and preferred assemblies for carrying out the invention are disclosed in connection with the accompanying drawings.

BRIEF DESCRIPTION OF THE DRAWINGS

The present invention will now be explained in more detail in the following with reference to preferred embodiments and to the accompanying drawings in which are shown.

DETAILED DESCRIPTION OF THE INVENTION

As used herein, the term 'proximal' refers to a region of the assembly/device or a location on the assembly/device which is closest to, for example, a medical practitioner using the assembly/device. In contrast to this, the term 'distal' refers to a region of the assembly/device which is farthest from the medical practitioner, for example, the distal region of a needle will be the region of a needle containing the needle tip which is to be inserted e.g. into a patient's vein.

Further, as used herein the term first and second are merely identifiers and do not necessarily limit and/or restrict the features with such identifiers. For example, when viewed from another perspective, the first arm may be called the second arm and vice-versa.

The various embodiments of present invention are directed to an IV catheter assembly including a tip protector assembly.

Figure 1A:
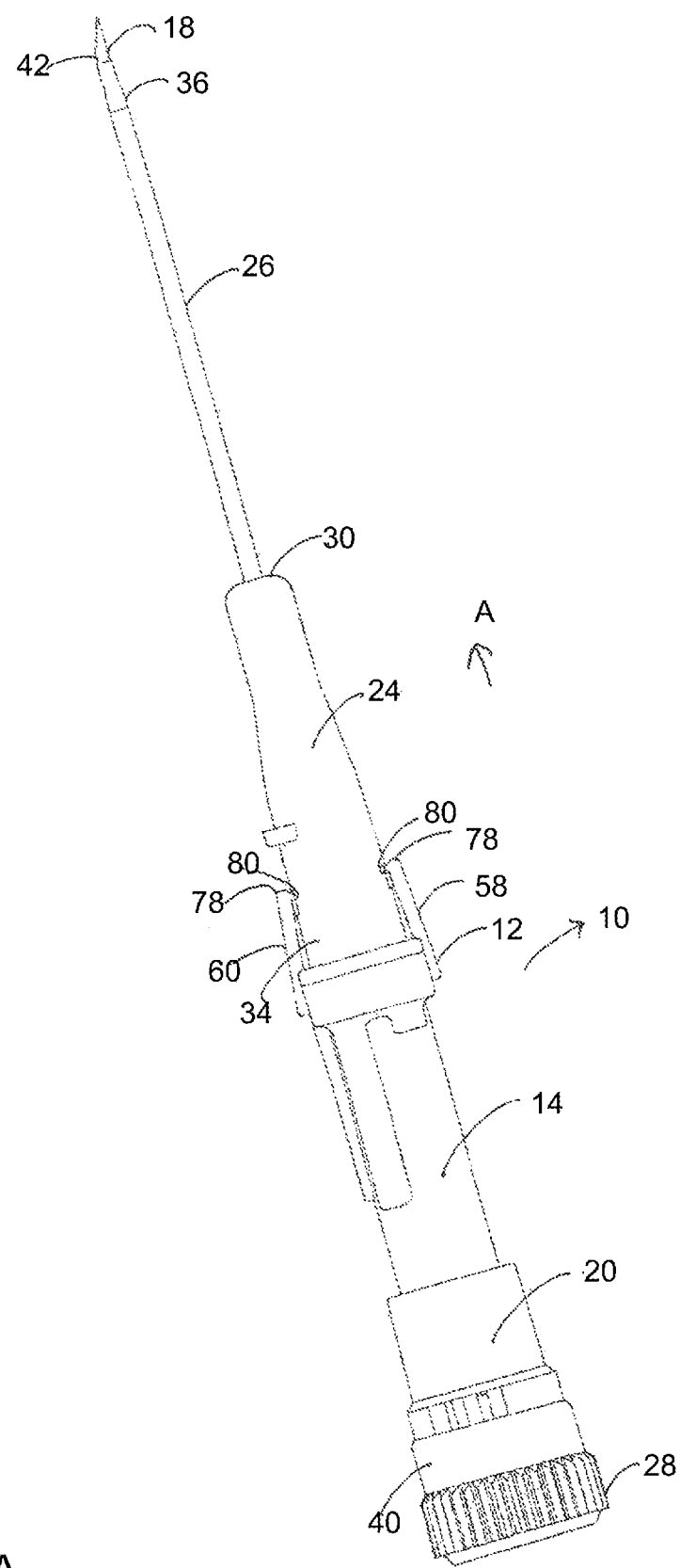
FIG. 1A illustrates an IV catheter assembly in accordance with the present invention illustrating the tip protector assembly in its ready position.
Figure 1B:
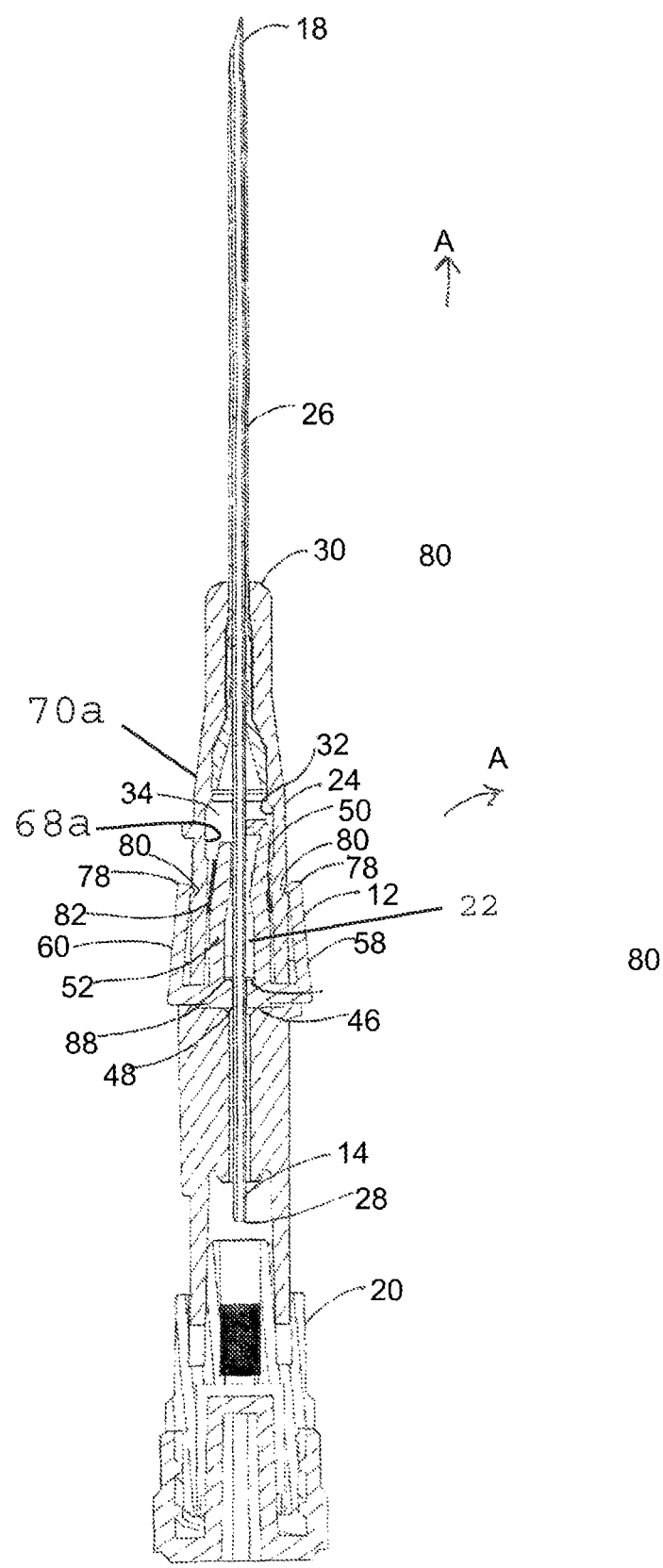
FIG. 1B is a sectional illustration of an IV catheter assembly in accordance with the present invention illustrating the tip protector assembly in its ready position.

FIGS. 1A and 1B show an IV catheter assembly 10 in accordance with the invention prior to use illustrating the tip protector assembly 12 being in its ready position. The catheter assembly 10 includes a catheter tube 26 having distal 30 and proximal 28 ends and a catheter hub 24 attached to the catheter tube 26 at the proximal end 28 of the catheter tube 26. The catheter hub 24 has an inner profile 32 which defines a chamber 34 of generally circular cross-section in which the tip protector assembly 12 is retained (as shown in FIG. 1B). In FIG. 1 only first 58 and second 60 retaining arms of the tip protector assembly 12 can be seen.

The IV catheter assembly 10 further includes a needle 14 extending through the catheter hub 24 and catheter tube 26 defining an axial direction A. The needle 14 has distal 30 and proximal 28 ends, wherein a sharp needle tip 18 is formed at the distal end 30 of the needle 14. A needle hub 20 is attached to the proximal end 28 of the needle 14. The needle shaft 16 has a generally constant principal profile, except for a change in profile 36, for example in the form of an enlargement 38 of the radial dimension of the needle 14 in at least one direction as compared to the principal profile. Preferably, the change in profile 36 is provided in the region closer to the proximal end 28 of the needle 14. The change in profile 36 may be defined as a needle section having a different dimension than the nominal diameter and may be created using various means and which forms an engagement means. The change in profile 36 can be made, for example, by crimping the needle shaft 16. The function of the engagement means will be discussed in more detail further below.

A port member (not shown) may be mounted on the catheter hub 24 at a proximal section 40 thereof, which makes it possible to connect, for example, a tube line to the catheter assembly 10 for collecting blood from a patient or delivering a fluid to be administered to a patient.

Figure 2:
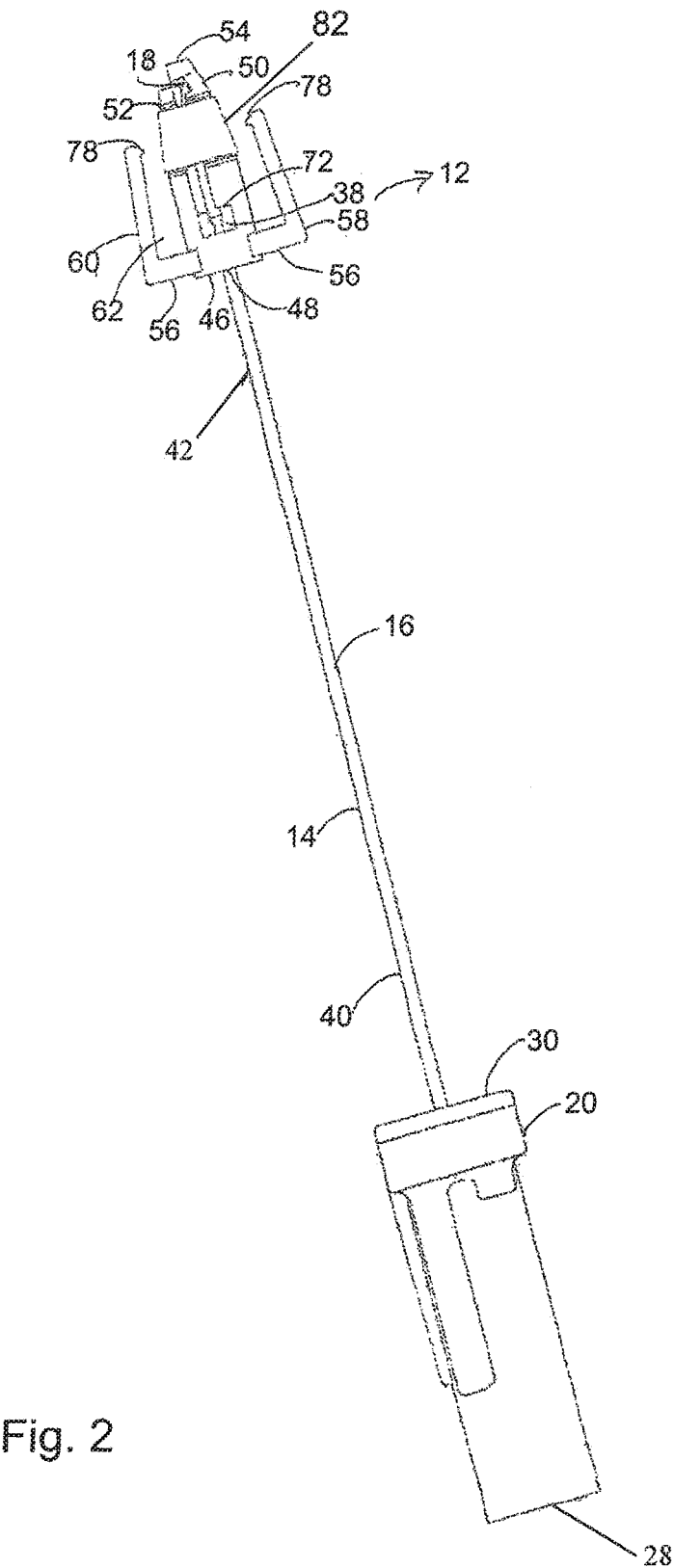
FIG. 2 illustrates a needle, needle hub and tip protector assembly in its protective position being removed from the IV catheter assembly of FIG. 1.
Figure 3A:
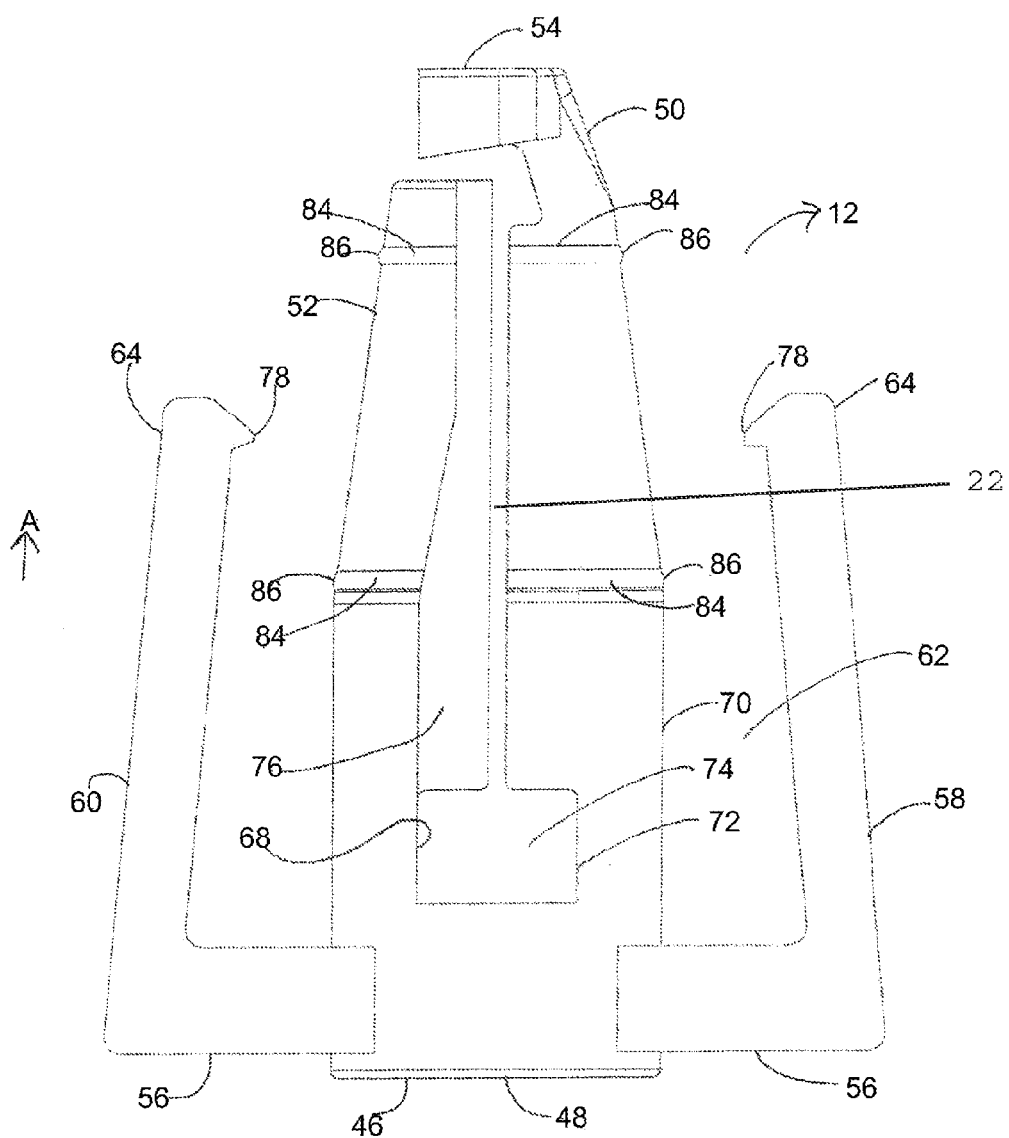
FIGS. 3A-3F illustrate the tip protector assembly of FIGS. 1A and 1B wherein the tension creating element has been omitted for the sake of clarity.
Figure 3B:
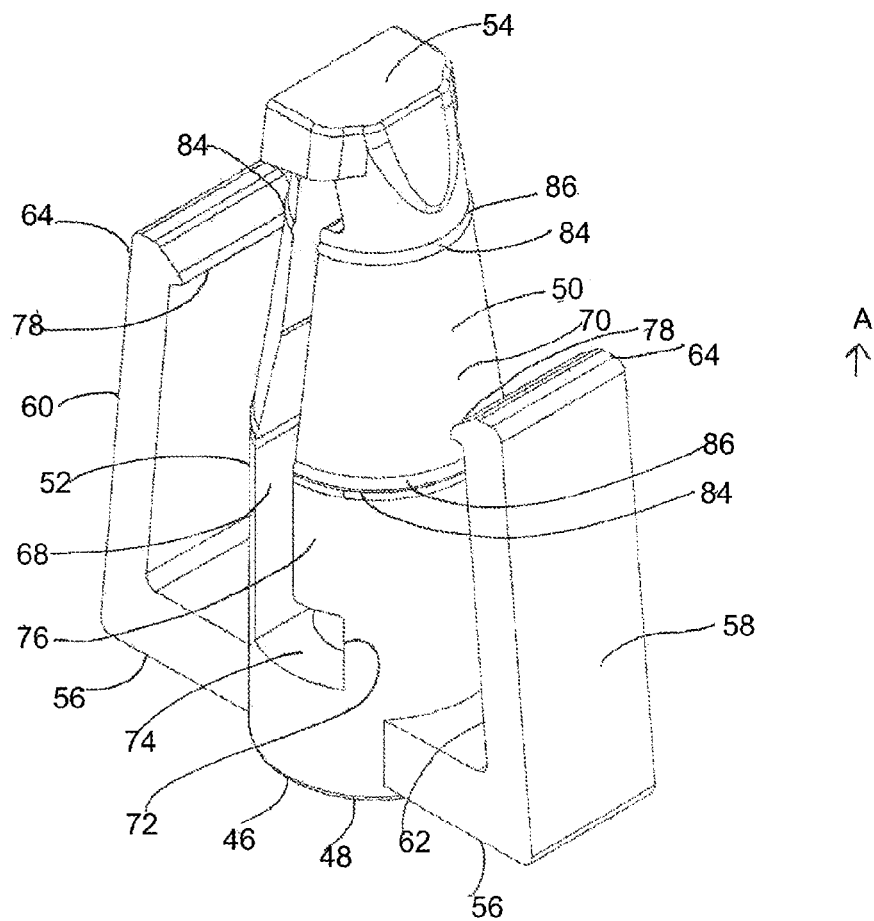
Figure 3C:
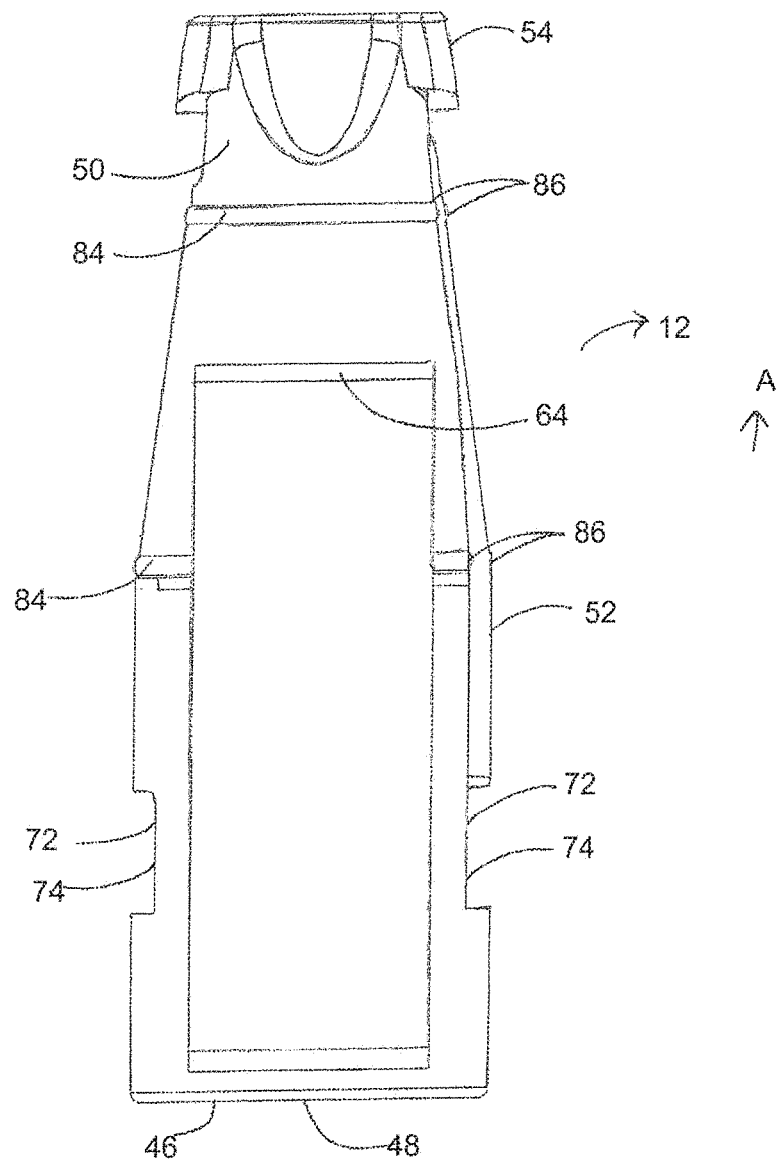
Figure 3D:
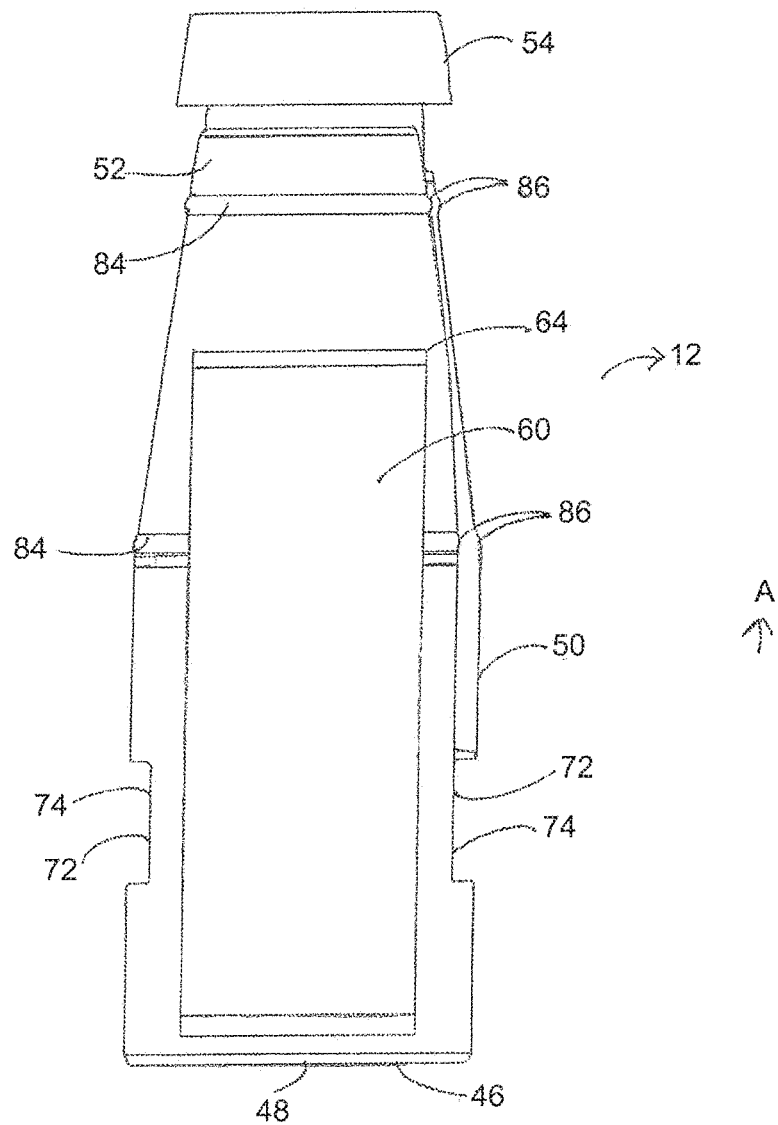
Figure 3E:
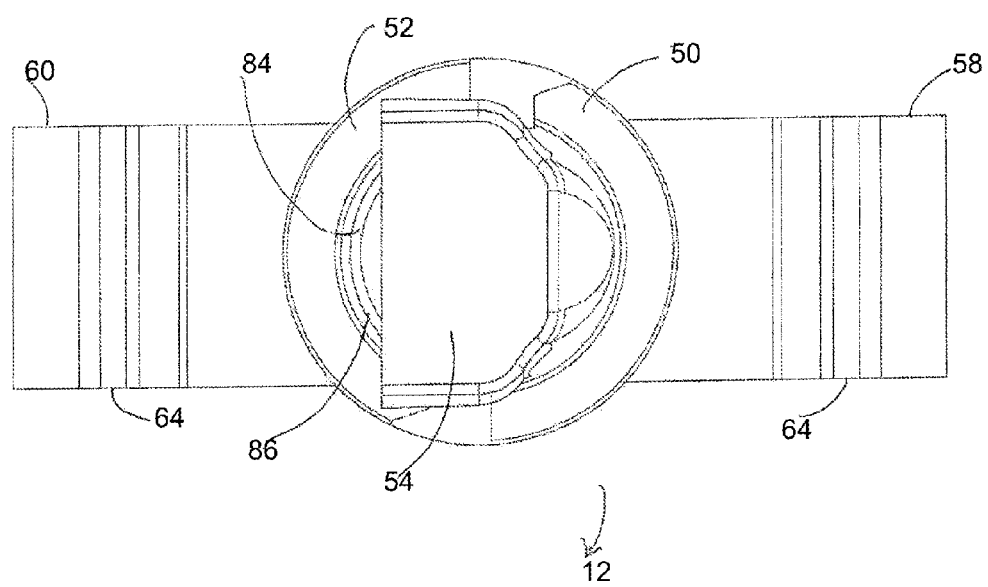
Figure 3F:
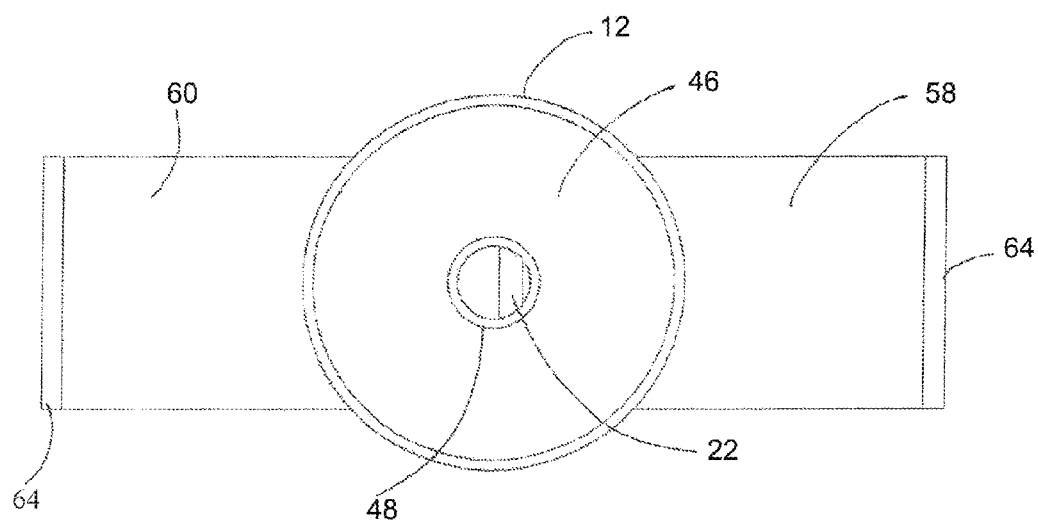

Prior to use of the catheter assembly 10 as shown in FIGS. 1A and 1B, the needle 14 extends all the way through the chamber 34 of the catheter hub 24 as well as the catheter tube 26 and the needle tip 18 protrudes from a distal end 30 of the catheter tube 26. As mentioned above, this position of the needle 14 is also referred to as the 'ready position' in this context. A tip protector assembly 12 is movably arranged on the needle shaft 16 such that a substantial portion thereof is retained in the chamber 34 defined by the catheter hub 24. The purpose of the needle tip protector assembly 12 is to cover the needle tip 18 after placement of the catheter tube 26 in and withdrawal of the needle 14 from the patient's vein. This position can be referred to as 'tip protecting position' (FIG. 2).

When the needle 14 is withdrawn from the catheter tube 26 and catheter hub 24 the needle shaft 16 moves relative to the tip protector assembly 12 being retained in the chamber 34 of the catheter hub 24 by the first retaining means provided on the first 50 and second 52 arms and first 58 and second 60 retaining arms in an engaging arrangement with the second retaining means provided inside and/or outside the catheter hub 24 defining a chamber 34. Once the needle tip 18 is received in the tip protector assembly 12 and passes the angled end section 54 of the first arm 50, at this point the angled end section 54 is no longer supported on the needle shaft 16 and a restoring force ensures that the first arm 50 of the needle 14 is moved back into alignment with the axial direction A into its tip protecting position so that the needle tip 18 is blocked by the angled end section 54 of the tip protector assembly 12. At the same time, it is to be understood that the change in profile 36 e.g. in the form of the enlargement 38 engages with the base portion 46 of the tip protector assembly 12 and in particular with the stopper element 88 therein such that the tip protector assembly 12 can be pulled out of the catheter hub 24 together with the needle 14. In such position, the first retaining means provided on the tip protector assembly 12 also disengage from the second retaining means provided inside and/or outside the catheter hub 24 by the pulling force acting on the tip protector assembly 12 via the needle 14 and the stopper element 88. An axial movement of the needle 14 relative to the tip protector assembly 12 is now limited, as the angled end section 54 blocks the needle tip 18 and the base portion 46 in particular the stopper element 88 therein prevents the needle tip 18 from being removed via the base portion 46 and thus the needle tip 18 is safely surrounded by the tip protector assembly 12, as is shown in FIG. 2.

As can be seen in more detail in FIGS. 3A-3F, 4A-4B and 5, the tip protector assembly 12 includes a base portion 46 at a proximal end 28 thereof. First 50 and second 52 arms extend from a distal side/end 30 of the tubular base portion 46 generally in the axial direction A. The base portion 46 has a thorough bore 48 for receiving the needle 14 extending in the axial direction A. The profile of the bore is adapted to the principle outer profile of the needle 14. The first arm 50 of the tip protector assembly 12 is longer than the second arm 52 and has a distal section which is angled towards the second arm 52 and substantially overlaps with the second arm 52, forming the angled end section 54 preferably having an undercut for catching the needle tip 18. In its ready position (FIG. 1A), the needle 14 extends completely through the tip protector assembly 12. In this position, the angled end section 54 of the first arm 50 is supported on the needle shaft 16 thereby deflecting the first arm 50 radially outwards.

In contrast to the first arm 50 and because of lack of distal angled end section 54, the second arm 52 has less deflectablity than the first arm 50 when the needle 14 extends through the tip protector assembly 12. Nevertheless, in order to facilitate deflectability of both the first 50 and second 52 arms, each of the at least one side of the inner walls 68 of the first 50 and second 52 arms of the tip protector assembly 12 has an internal recess 72 close to the base portion 46 thereof forming a cavity or cut out 74. The extension of the region above the said internal recess 72 towards the distal end 30 in the axial direction A forms protective side-flap 76 (FIGS. 4A and 4B) in at least one side thereof providing an enclosure for the needle 14 passing therethrough in both the first 50 and second 52 arms. The protective side-flaps 76 provided in at least one side of the first 50 and second 52 arms surround the needle shaft 16 when passing through the first 50 and second 52 arms. Moreover, the protective side-flaps 76 help prevent the needle tip 18 from protruding sideways out of the tip protector assembly 12, thereby further increasing the protective function thereof. It is to be understood that the protective side-flap 76 can be provided on the either sides of the first 50 and second 52 arms in a similar manner. Further, such internal recess 72 can be formed both on the inner 68 and outer 70 walls of the first 50 and second 52 arms or in a combination of the inner 68 and outer wall 70 of the first 50 and second 52 arms.

The tip protector assembly 12 is also provided with first 58 and second 60 retaining arms in order to facilitate further the retention of the tip protector assembly 12 in the chamber 34 of the catheter hub 24, and in particular to prevent removal of the tip protector assembly 12 from the catheter hub 24 upon withdrawal of the needle 14 before the needle tip 18 has been safely received in the tip protector assembly 12. The first 58 and second 60 retaining ai ins thus prevent the tip protector assembly 12 retained in the catheter hub 24 from moving in a radial direction within the chamber 34.

The first 58 and second 60 retaining arms as shown in greater detail in FIGS. 3A, 3B, 4A, 4B and 5 are connected to the base portion 46 of the tip protector assembly 12 by a transverse segment 56 extending in a direction opposing each other. The distal ends 30 of the transverse segments 56 of the first 58 and second 60 retaining arms are angled and extend distally from the transverse segments 56 and are slightly tilted towards the first 50 and second 52 arms. Preferably, the first 58 and second 60 retaining arms form an angle in the range between 0° and 10° with the axial direction A, providing an open space 62 between the first retaining al in 58 and first arm 50 and second 60 retaining arms and second arm 52 of the tip protector assembly 12.

The distal ends 30 of the first 58 and second 60 retaining arms are also provided with first retaining means in the form of one or more retaining protrusions 78 on retaining arm ends 64, for example, at least one hook or lug like retaining protrusion 78. When the tip protector assembly 12 is in the ready position, first retaining means lockingly engage with the corresponding second retaining means in the form of one or more retaining depressions 80, for example at least a pair of grooves or recesses in a direction opposing each other on the outer wall 70a of the catheter hub 24. Because of the engagement between the first retaining means and second retaining means, the tip protector assembly 12 is prevented from axial movement relative to the catheter hub 24 and effectively retained in the catheter hub 24 until a pulling force exerted by the needle 14 on the base portion 46 of the tip protector assembly 12 via the change in profile 36 of the needle 14 upon withdrawal of the needle 14 from the catheter becomes great enough to disengage the first 58 and second 60 retaining arms from the second retaining means of the catheter hub 24.

It is to be noted that instead of the retaining depressions 80 provided on the outer wall 70a of the catheter hub 24 it is also possible to provide one or more retaining protrusions 78 or combination of either a protrusion 86 or a recess in the outer wall 70a of the catheter hub 24 to engage with the first 58 and second 60 retaining arms. Likewise, instead of the retaining protrusions 78 provided on the first 58 and second 60 retaining arms it is also possible to provide one or more retaining depressions 80 or combination of either a retaining protrusion 78 or a depression to engage with the catheter hub 24.

In order to enhance further the retaining effect of the tip protector assembly 12 in the catheter hub 24, the distal ends 30 of the first 50 and second 52 arms are provided with first retaining means (not shown). The first retaining means include one or more retaining protrusions 78, for example disc-like retaining protrusion 78 or annular disc like protrusion 86 or at least part annular disc like protrusion 86 provided in the region of the distal ends 30 of the first 50 and second 52 arms. According to a preferred embodiment, the retaining protrusion 78 is of part-circular, in particular semicircular shape. More specifically, the retaining protrusion 78 may have generally parallel proximal and distal faces and/or convex, in particular part-cylindrical, peripheral surface. The retaining protrusions 78 are adapted to engage with second retaining means provided in the inner wall 68a of the catheter hub 24 when the tip protector assembly 12 is in its ready position. The second retaining means include one or more retaining depressions 80 for example, a recess or annular recess/groove or at least part annular recess/groove formed on the inner circumferential wall of the catheter hub 24.

In a preferred alternative, the first retaining means provided on the first 50 and second 52 arms may be one or more retaining depressions 80 and second retaining means provided on the inner wall 68a of the catheter hub 24 may be one or more retaining protrusions 78. As a further alternative, the first and second retaining means may also be formed by a combination of retaining protrusions 78 and retaining depressions 80.

As shown in FIGS. 3A, 3B, 4A, 4B and 5, the base portion 46, the first 50 and second 52 arms, the first 58 and second 60 retaining arms are integrally formed, for example, from a plastic material by way of injection molding. However, it is to be understood that this integral design is not compulsory. Instead, one or more of the named components could be made of a material that is different from the material of the other components, for example of metal material, and this component could be attached to the other components, for example, by gluing, soldering, welding or the like.

Even though the first 50 and second 52 arms are have certain elastic properties, a tension creating element 82, for example a rubber band, may surround preferably a distal section of the first 50 and second 52 arms are such that deflection of at least the first arm 50 occurs mainly against a restoring force of the tension creating element 82. One or more protrusions 86 forming tapered outer surfaces 84 extending along the outer periphery of the first 50 and second 52 arms are provided in order to position the tension creating element 82 on the first 50 and second 52 arms are (FIGS. 3A-3D). Because of the tapered outer surfaces 84 the tension creating element 82 is prevented from sliding off the distal sections of the first 50 and second 52 arms are, when the first 50 and second 52 arms are spread apart against a restoring force of the tension creating element 82. In a preferred alternative, the tension creating element 82 may not be a separate component of the tip protector assembly 12 and can be integrally made therein.

In another preferred alternative, the tension creating element 82 partly surrounds the first 50 and second 52 arms (not shown) of the tip protector assembly 12 i.e. instead of surrounding the two arms the tension creating elements 82 biases the two arms by a linear biasing action. In another preferred alternative, the tension creating element 82 have the structure forming a link connecting the said first 50 and second 52 arms (not shown) and which may be positioned and/or arranged in at least one of the either sides of first 50 and second 52 arms of the tip protector assembly 12. In yet another preferred alternative, the tension creating element 82 may have the structure forming a link connecting the said first 50 and second 52 arms (not shown) and which may be positioned and/or arranged in both sides of first 50 and second 52 arms of the tip protector assembly 12.

Figure 4A:
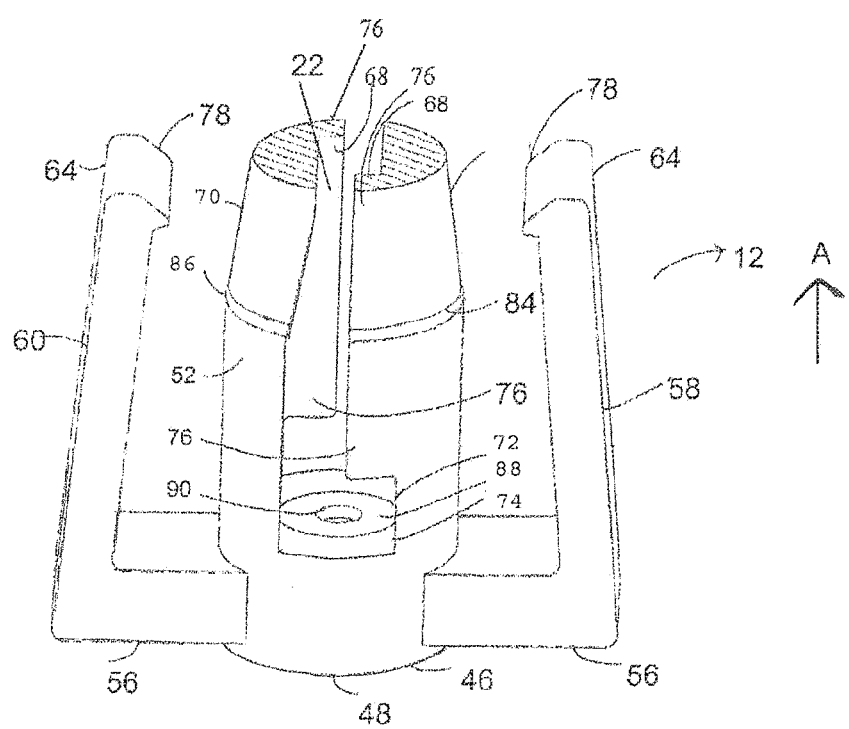
FIGS. 4A-4B illustrate two sectional illustrations of the details of tip protector assembly of FIGS. 3A-3F wherein the tension creating element has been omitted for the sake of clarity.
Figure 4B:
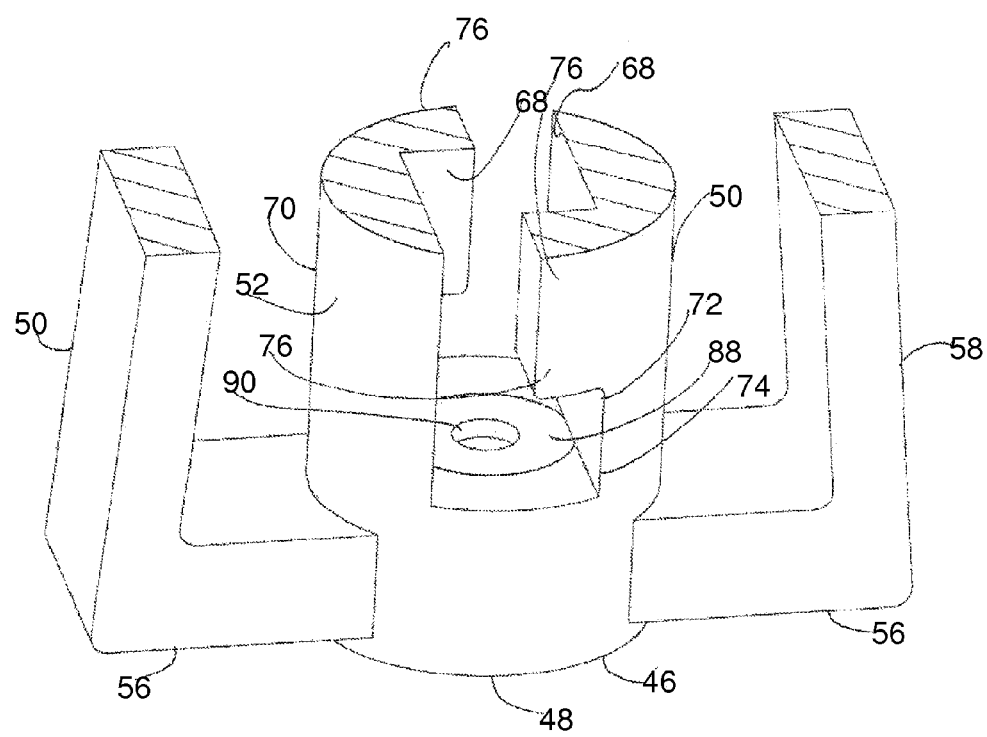
Figure 5:
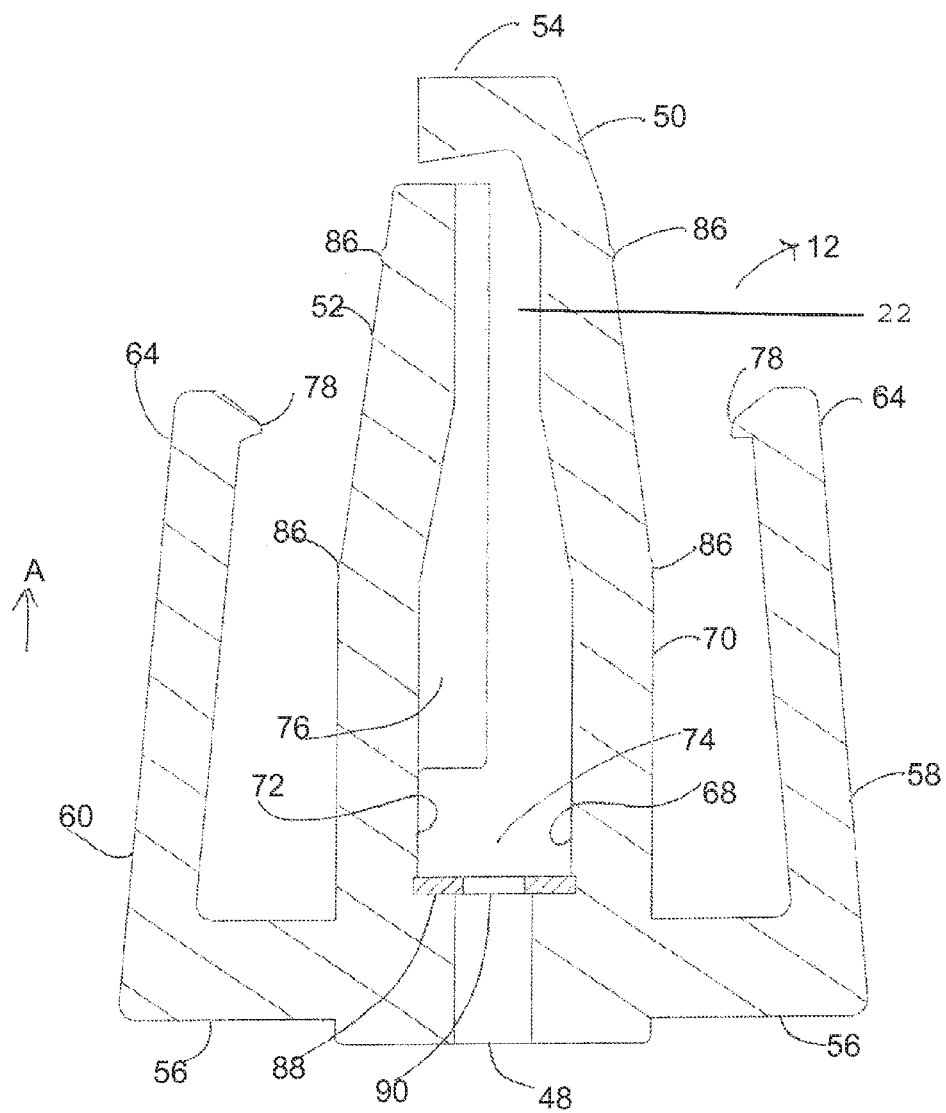
FIG. 5—illustrate sectional illustration of tip protector assembly of FIGS. 3A-3F wherein the tension creating element has been omitted for the sake of clarity.

As is best seen in FIGS. 4A, 4B and 5, a stopper element 88 is provided in the base portion 46 or on the distal side/end of the base portion 46, for example by insert molding. The stopper element 88 has an axial bore 90 which is aligned with the thorough-bore of the base portion 46. The axial bore 90 has a circular cross-section with its diameter being slightly larger than the principle diameter of the proximal section 40 of the needle shaft 16 relative to the stopper element 88. More specifically, the cross-section of the axial bore 90 of the stopper element 88 is adapted to the principal profile of the needle shaft 16 such that the stopper element 88 can slide along the needle shaft 16 with minimum friction. At the same time the diameter of the axial bore 90 is not only smaller than that of the needle passage 22 but also smaller than the maximum dimension of the change in profile 36 of the needle shaft 16, e.g. in the form of enlargement 38, in order to prevent the enlargement 38 from passing through the axial bore 90 and, thus, to prevent the tip protector assembly 12 from sliding off the needle 14.

Preferably, such a stopper element 88 would be made of a second material of a greater hardness and/or stiffness different from the first material of the base portion 46, such that the stopper element 88 withstands greater force exerted by the change in profile 36 of the needle 14 upon withdrawal of the needle 14 from the catheter tube 26, thereby more effectively preventing the change in profile 36 of the needle 14 from passing through the base portion 46 and thus more effectively preventing the tip protector assembly 12 from sliding off the needle 14. Preferably, the stopper element 88 has a disk-like shape, similar to a washer or ring and is made of hard plastic, metal or ceramic and it can also be made out of any other material which is stiff and which cannot easily be distorted.

The fact that the stopper element 88 is made from a second material which is harder and less easily distortable than the first material of the base portion 46, has the effect that the tip protector assembly 12 is secured more effectively on the needle shaft 16 and can be retained even if excessive external force is applied when pulling on the needle 14, as the change in profile 36 in the form of, for example an enlargement 38 acting as engagement means is prevented from being pulled through the base portion 46 of the tip protector assembly 12. Hence, it is less likely that the tip protector assembly 12 is removed from the needle 14 tip accidentally and, as a result, the tip protector assembly 12 provides a better protection against accidental pricking and thus increased safety for the person handling the catheter assembly 10.

Further, it is to be understood, that the stopper element 88 need not be arranged in the base portion 46 itself, but can also be arranged at the distal side/section thereof between the first 50 and second 52 arms of the tip protector assembly 12. Thus, the position of the stopper element 88 in between the first 50 and second 52 arms can be selected freely.

As a preferred alternative, the stopper element 88 may also be arranged loosely on the needle 14 between the two arms 50, 52 of the tip protector assembly 12 and floating on the needle shaft 16 and can be held in the area defined by the internal recess 72 of the first 50 and second 52 arms (not shown). As such the stopper element 88 may be formed by a tube-like element. It can be held by holding means, like one or more retaining protrusions 78 or retaining depressions 80 in a predetermined section of the tip protector assembly 12, for example in a region proximal to the base portion 46 of the tip protector assembly 12. Alternatively, the stopper element 88 can be arranged in floating condition in a pre-determined section in between the first 50 and second 52 arms of the tip protector assembly 12 anywhere in between the proximal section 40 and distal section 42 thereof along the line of needle passage 22 configured therein.

Figures 6A, 6B, 6C:
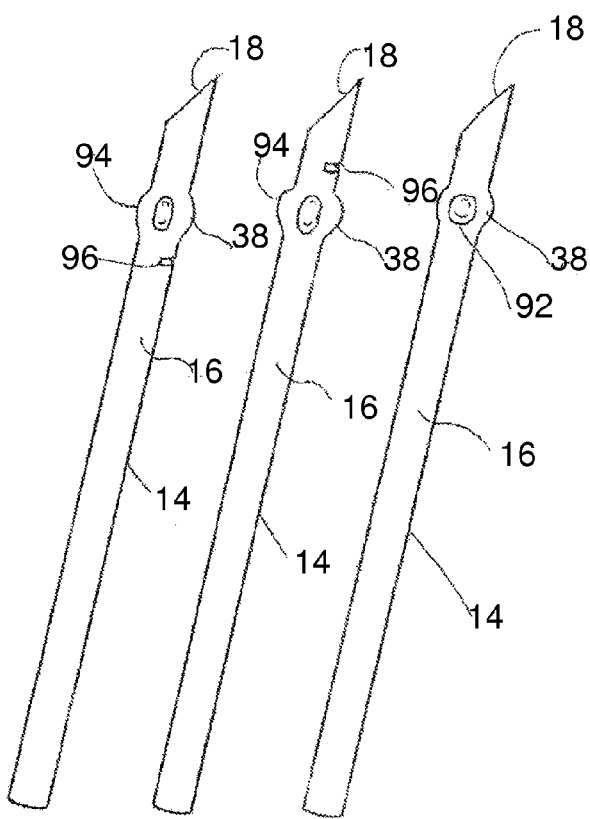
FIG. 6A-6C are illustrations of different embodiments of the needles.

FIG. 6A shows an embodiment of a needle 14 having a needle shaft 16, a needle tip 18 and a change in profile 36 in the form of an enlargement 38 formed for example, by a crimp. The crimp is made by a local depression 92 such that lateral protrusions 94 resulting from the crimping process. Preferably, the crimping process is controlled such that the internal cross-sectional area of the needle 14 is not reduced substantially such that the internal profile of the needle shaft 16 is not affected.

FIG. 6B shows the needle 14 according to FIG. 7A, however having a slit forming an opening 96 arranged slightly distally from the change in profile 36, such that it is still arranged within the catheter tube 26 in the ready position. The opening 96 just extends over about 0.5 mm in axial direction A and provides a through hole through the needle 14 wall. Thereby, an early blood flashback within the transparent catheter tube 26 can be achieved when the needle 14 is positioned into the patient's vein. Based on this blood flashback, the practitioner can see right after puncturing the patient whether the needle 14 has been positioned correctly due to a small amount of patient's blood oozing out the space between the needle shaft 16 and the transparent catheter tube 26.

FIG. 6C shows the needle 14 according to FIG. 6B, however with the slit forming an opening 96 arranged proximally from the change in profile 36. The opening 96 is dimensioned such that it does not affect the functioning of the tip protector assembly 12.

It is to be understood that securing the tip protector assembly 12 partially in the chamber 34 of the catheter hub 24 by means of first and second retaining means with the catheter hub 24 is a simple measure achieving a safe seat of the tip protector assembly 12 and which effectively prevents accidental removal of the tip protector assembly 12 from the catheter chamber 34 prior to the needle tip 18 being received in the tip protector assembly 12. Not only this arrangement ensures correct protective function of the tip guard assembly 12 but also ensures that the tip protector assembly 12 is secured steadily inside the catheter hub 24 removing entirely the problem of pre-mature release when pulling force applied on the needle 14 to withdraw/disengage the needle hub 20 from the catheter hub 24. Hence, the risk of premature release of the tip protector assembly 12 from the catheter hub 24 during withdrawal of the needle 14 from the catheter and catheter hub 24 and, thus, the risk of accidental pricking by the needle 14 is reduced.

Moreover, the IV catheter assembly 10 including tip protector assembly 12 of the invention can be manufactured at reduced costs while at the same time the safety of the IV catheter assembly 10 is increased. The IV catheter assembly 10 including the tip protector assembly 12 is particularly inexpensive to manufacture if the base portion, the first 50 and second 52 arms, first 58 and second 60 retaining arms having retaining arm ends 64 are integrally made from a first material. The first material may, for example, be a plastic material. Thus, the base portion 46, the first 50 and second 52 arms and the first 58 and second 60 retaining arms could be manufactured by injection moulding.

Alternatively, the base portion 46, one of the first 50 and second 52 arms and the first 58 and second 60 retaining arms could be integrally made from a first material, for example a plastic material and the other one of the first 50 and second 52 arms and the first 58 and second 60 retaining arms could be made from a second material different from said first material. For example, said one of the first 50 and second 52 arms could include a strip of material having spring-like properties, e.g. a strip of sheet metal or any other suitable material.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. For example, the tip protector assembly 12 of the present invention can also be adapted such that without including the stopper element 88. In this case, the outer profile of the enlargement 38 on the needle shaft 16 must be greater than the profile of the thorough-bore 48 provided in the base portion 46 of the tip-protector assembly 12, in order to prevent the tip protector assembly 12 from sliding off the needle 14 in a distal direction. Thus, from the foregoing description, it will be apparent to one of ordinary skill in the art that many changes and modifications can be made thereto without departing from the spirit or scope of the invention as set forth herein.

Accordingly, it is not intended that the scope of the foregoing description be limited to the exact description set forth above, but rather that such description be construed as encompassing all of the features of patentable novelty that reside in the present invention, including all the features and embodiments that would be treated as equivalents thereof by those skilled in the relevant art. Thus, it is intended that the scope of the present invention herein disclosed should not be limited by the particular disclosed embodiments described above.

REFERENCE NUMERALS

- 10 IV catheter assembly
- 12 tip protector assembly
- 14 needle
- 16 needle shaft
- 18 needle tip
- 20 needle hub
- 22 needle passage
- 24 catheter hub
- 26 catheter tube
- 28 proximal end
- 30 distal end
- 32 inner profile
- 34 chamber
- 36 change in profile
- 38 enlargement
- 40 proximal section
- 42 distal section
- 46 base portion
- 48 thorough bore
- 50 first arm
- 52 second arm
- 54 angled end section
- 56 transverse segment
- 58 first retaining arm
- 60 second retaining arm
- 62 open space
- 64 retaining arm ends
- 68 inner walls of the first and second arms
- 68a inner wall of the catheter hub
- 70 outer walls of the first and second arms
- 70a outer wall of the catheter hub
- 72 internal recess 74 cavity or cut out
76 protective side flap
78 retaining protrusion
80 retaining depression
82 tension creating element
84 tapered outer surface
86 protrusion
88 stopper element
90 axial bore
92 local depression
94 lateral protrusion
96 opening
A axial direction

What is claimed is:

1. A safety IV catheter assembly comprising:
   a needle hub;
   a catheter hub defining a chamber, said catheter hub having a pair of retaining structures provided outside the chamber of the catheter hub that are exposed when the catheter hub engages the needle hub;
   a needle extending from the needle hub and through the catheter hub and having a sharp tip and a section having a change in profile provided between the proximal and distal ends of the needle
   a tip protector assembly movably arranged on the needle such that the tip protector assembly is retained partially and/or completely in the chamber of the catheter hub, said tip protector assembly including:
      a base portion having a needle passage with a thorough bore extending therethrough in an axial direction;
      first and second arms extending substantially parallel to each other in the axial direction from the distal section of the base portion and forming a needle passage therebetween for permitting passage of the needle;
      at least one tension creating element surrounding partially and/or completely the said first and second arms in a region proximal to the distal ends thereof;
      at least one stopper element arranged in the base portion having an axial bore with a dimension adapted to engage the section of the needle having the change in profile;
      at least one pair of first and second retaining arms connected to the base portion by transverse segments extending therefrom and in a direction opposing each other; and
      a respective first retaining means provided on each one of the retaining arms, each one of the first retaining means configured in an arrangement respectively engaging with a respective one of the exposed retaining structures provided on the catheter hub for retaining the tip protector assembly in the chamber as long as one of the first or second arms is in a deflected state resting over the needle shaft.

2. The IV catheter assembly as claimed in claim 1, wherein the first retaining means include one or more retaining protrusions or retaining depressions or combination thereof arranged in the region of the distal ends of the first and second retaining arms.

3. The IV catheter assembly as claimed in claim 1, wherein the first retaining means include one or more retaining protrusions or retaining depressions or combination thereof arranged in the distal section of the first and second arms in a direction opposing each other.

4. The IV catheter assembly as claimed in claim 1, wherein the retaining structures include one or more retaining depressions or retaining protrusions or combination thereof arranged in the outer wall of the catheter hub in a direction opposing each other.

5. The IV catheter assembly as claimed in claim 1, wherein the retaining structures include one or more retaining depressions or retaining protrusions or combination thereof arranged in the inner wall of the catheter hub in a direction opposing each other.

6. The IV catheter assembly as claimed in claim 1, wherein at least one side of the inner wall of the first and second arms of the tip protector assembly has internal recess close to the base portion thereof forming a cavity or cut out.

7. The IV catheter assembly as claimed in claim 6, wherein the extension of the region above the internal recess towards the distal end in the axial direction A forms protective side-flaps in at least one side thereof providing an enclosure for the needle passing therethrough.

8. The IV catheter assembly as claimed in claim 1, wherein the distal ends of the transverse segments are angled and extend distally from the transverse segments and are slightly tilted towards the first and second arms forming an angle in the range between 0° to 10°.

9. The IV catheter assembly as claimed in claim 2, wherein the retaining protrusion is a hook or lug-like retaining protrusion or disc-like retaining protrusion or annular disc like retaining protrusion or at least part annular disc-like retaining protrusions or combination thereof.

10. The IV catheter assembly as claimed in claim 2, wherein the retaining depression is a retaining recess/groove or annular retaining recess/groove or at least part annular recess/groove or combination thereof.

11. The IV catheter assembly as claimed in claim 1, wherein either of the first and second arms or both may be made of a resilient material or plastic material or metal material or combination thereof.

12. The IV catheter assembly as claimed in claim 1, wherein the first arm includes a first free end and the second arm includes a second free end extending generally axially in a distal direction from the base portion.

13. The IV catheter assembly as claimed in claim 12, wherein the first free end extends beyond the second free end and overlaps the second free end by an angled end section.

14. The IV catheter assembly as claimed in claim 13, wherein the length and width of the angled end section are larger than the maximum outer profile of the needle and/or its diameter and is adapted to confine the needle tip within a tip holding space.

15. The IV catheter assembly as claimed in claim 1, wherein the change in profile is formed by an enlargement of the radial dimension of the needle in at least one direction as compared with a principal profile of the needle having an outer profile one dimension of which is larger than a maximum dimension of the profile of the thorough bore.

16. The IV catheter assembly as claimed in claim 15, wherein the enlargement is a crimp or a sleeve or a bulge or a section of the needle with added material or combinations thereof.

17. The IV catheter assembly as claimed in 1, wherein the stopper element is arranged being integrally formed within the base portion such that its axial-bore is in general alignment with the needle passage and is made of a second material different from a first material of the base portion.

18. The IV catheter assembly as claimed in claim 1, wherein the stopper element surrounds the needle and is a disk or a ring or a washer or a tube.

19. The IV catheter assembly as claimed in claim 1, wherein the stopper element partly surrounds the needle and is a slotted disk, ring or tube.

20. The IV catheter assembly as claimed in claim 17, wherein the stopper element defines an axial bore having a cross-section adapted to the principal profile of the needle but being smaller than the radial dimension of the change in profile.

21. The IV catheter assembly as claimed in claim 1, wherein needle shaft is formed with a slit forming an opening arranged distally or proximally from the change in profile.

22. The IV catheter assembly as claimed in claim 1, wherein the tension creating element have the structure forming a link connecting the said first and second arms and arranged in at least one of the either sides of first and second arms of the tip protector assembly.

23. A safety IV catheter assembly comprising:
a catheter tube having a distal end and a proximal end;
a needle hub;
a catheter hub having a distal end and a proximal end, wherein the distal end is joined to the said catheter tube and the proximal end defines a chamber, said catheter hub having a pair of retaining structures provided on an outer surface of the catheter hub that are exposed when the catheter hub engages the needle hub;
a needle extending from the needle hub and through the catheter hub and the catheter tube having opposite proximal and distal ends defining an axial direction A, wherein the proximal end is joined to the needle hub and the distal end having a sharp tip and a section having a change in profile provided between the proximal and distal ends of the needle;
a tip protector assembly movably arranged between the catheter hub and needle hub on the needle such that the tip protector assembly is retained partially and/or completely in the chamber of the catheter hub, said tip protector assembly including:
a base portion in the region of the proximal end of the tip protector having a needle passage with a thorough bore extending in the axial direction A from a proximal side of the base portion to a distal side of the base portion;
first and second arms, said first arm including an end section at one end, said arms extending substantially parallel to each other in the axial direction A from the distal section of the base portion and forming a needle passage therebetween coaxial with said through bore for permitting passage of the needle;
at least one tension creating element surrounding partially and/or completely the said first and second arms in a region proximal to the distal ends thereof;
at least one stopper element arranged in the base portion having an axial bore with a dimension adapted to engage the section of the needle having the change profile;
at least one pair of retaining arms connected to the base portion by transverse segments extending therefrom and in a direction opposing each other; and
a respective first retaining means provided on each one of the retaining arms, each one of the first retaining means configured in an arrangement respectively engaging with a respective one of the exposed retaining structures provided on the catheter hub for retaining the tip protector assembly in the chamber as long as the first and second arms are in a deflected state resting over the needle shaft, wherein
at least the base portion and the first and second arms of said tip protector assembly are integrally formed of a non-metallic material.

* * * * *